United States Patent [19]
Yamagishi et al.

[11] Patent Number: 4,885,469
[45] Date of Patent: Dec. 5, 1989

[54] INFRARED GAS ANALYZER

[75] Inventors: Yutaka Yamagishi; Kenji Takeda, both of Kyoto, Japan

[73] Assignee: Horiba Ltd., Kyoto, Japan

[21] Appl. No.: 194,491

[22] Filed: May 16, 1988

[30] Foreign Application Priority Data

Jun. 10, 1987 [JP] Japan ................... 62-145959

[51] Int. Cl.$^4$ ............................................. G01N 21/26
[52] U.S. Cl. ..................................... 250/345; 250/343
[58] Field of Search ................... 250/338.5, 345, 343

[56] References Cited
U.S. PATENT DOCUMENTS 3,869,613  3/1975  Link et al. ........................... 250/343
4,236,827 12/1980  Horiba et al. ....................... 250/343
4,794,255 12/1988  Miyatake et al. .................. 250/345

Primary Examiner—Janice A. Howell
Assistant Examiner—T. Nguyen
Attorney, Agent, or Firm—Price, Gess & Ubell

[57] ABSTRACT

An infrared gas analyzer reduces influenced results from interfering gases by utilizing a first filter system intermediate a light source and a gas cell in which the sample is located. The filter system passes light having wavelengths within absorption bands of the gas to be measured. It also reflects light having wavelengths outside of the absorption bands. A second filter system is also intermediate the light source and the first filter system. The second filter system absorbs light having wavelengths within absorption bands of an interfering component gas.

13 Claims, 3 Drawing Sheets

INFRARED GAS ANALYZER

BACKGROUND OF THE INVENTION

1. Field of the Invention

The present invention generally relates to an infrared gas analyzer for detecting gases contained in air, exhaust gas, and the like. More specifically, it relates to an improved infrared gas analyzer that prevents influenced results by interfering gases.

2. Description of Related Art

As to an infrared gas analyzer for detecting gases contained in air, exhaust gas, and the like, in the case where interfering component gases having an absorption wavelength range partially overlapping a wavelength range of a gas to be measured are contained in a sample gas, an infrared gas analyzer capable of preventing an influence by the interfering component gases comprising an interference filter as shown in FIG. 2 has been known.

This gas analyzer comprises a reference cell 1, in which a reference gas is enclosed. A sample cell 2, in which a sample gas is to be supplied, is disposed in parallel. The sample cell 2 is provided with a supply port 3a for supplying the sample gas and an exhaust port 3b for exhausting the sample gas. Reference numerals 4a, 4b designates a light source disposed on one side of the reference cell 1 and the sample cell 2, respectively. Reference numeral 5 designates a detector, such as condenser microphone, disposed on the other side of the reference cell 1 and the sample cell 2.

Reference numeral 6 designates a chopper disposed between the reference cell 1 and the sample cell 2 and the light sources 4a, 4b. Reference numerals 7a, 7b designates interference filters disposed between the reference cell 1 and the sample cell 2 and the detector 5. The filters 7a, 7b pass radiation including a wavelength range in any absorption bands of the gas to be measured but reflect radiation that is in a non-absorbing wavelength range. Reference numeral 9 designates a preamplifier.

With this infrared gas analyzer, a radiation emitted from the light sources 4a, 4b is intermittently incident upon the reference cell 1 and the sample cell 2 by rotating the chopper 6. Thereupon, a part of the radiation is absorbed by a gas enclosed in the reference cell 1 and the sample cell 2, respectively, so that the energy of radiation incident upon the detector 5 from the reference cell 1 is different from that from the sample cell 2. The sample gas is analyzed on the basis of this difference in energy of radiation.

And, radiation including any wavelengths within the absorption bands of the interfering gases contained in the sample gas supplied in the sample cell 2 and incident upon the reference cell 1 and the sample cell 2 are reflected by the interference filter 7 to prevent them from being incident upon the detector 5, whereby the influences of the interfering component gases are reduced.

Also an infrared gas analyzer shown in FIG. 3 has been known. In this infrared gas analyzer, the interference filter 7 in the gas analyzer shown in FIG. 2 is replaced with gas filter cells 8a, 8b for absorbing the interfering component gases. Other constructions of FIG. 3 are the same as in the gas analyzer shown in FIG. 2, so that they are marked with the same reference numerals and marks.

In the gas analysis by this gas analyzer (FIG. 3), radiation having wavelengths of the absorption bands of the interfering components contained in the sample gas and incident upon the reference cell 1 and the sample cell 2 are absorbed by the gas filter cell 8 to reduce the influences of the interfering components.

Also, an infrared gas analyzer of an interference compensation type as shown in FIG. 4 has been known. In this gas analyzer, a detector 5a is adapted to be able to pass radiation therethrough. An interference-compensating detector 5b, upon which the radiation passing through the detector 5a is incident, is provided. A subtracter 10 for subtracting an output of the interference-compensating detector 5b from an output of the detector 5a is provided in the gas analyzer as shown in FIG. 4.

Other constructions are the same as in the gas analyzer shown in FIG. 2, so that they are marked with the same reference numerals and marks.

With the conventional infrared gas analyzer as shown in FIG. 2, a reflection factor of the interfering component of radiation by the interference filter 7 is high, so that the influences of the interfering component radiation can be reduced.

Here, the transmission and reflection of the radiation by the interference filter in the case where the window on the side of the detector of the gas cell S is replaced with the interference filter f, as shown in FIG. 5, is investigated.

Radiation which shall be illustrated by a light beam $I_o$ emitted from a light source L passes through the window W of the gas cell S to enter the gas cell S. After a part of the light $I_o$ is absorbed by the component to be measured contained in the gas cell S, the remaining light $I_o$ passes through the interference filter F to enter the detector (not shown).

The total transmission quantity $T_1$ of radiation having a wavelength range capable of passing through the interference filter F at this time is expressed by the following equation (1):

$$T_1 = I_o \frac{tf \cdot tw \exp(-\epsilon cl)}{1 - rw \cdot rf [\exp(-\epsilon cl)]^2} \quad (1)$$

Even though tf is replaced with tw and rf is replaced with rw, it is one and the same thing, so that the transmission quantity of radiation capable of passing through the interference filter has nothing to do with their incident direction. That is to say, it is one and the same thing even though the radiation is are incident from the side of the interference filter F.

On the other side, the total reflection quantity R of radiation having a reflection wavelength range of the interference filter is expressed by the following equation (2):

$$R = I_o \left( rf - \frac{rw \, tf^2 [\exp(-\epsilon cl)]^2}{1 - rw \cdot rf [\exp(-\epsilon cl)]^2} \right) \quad (2)$$

The quantity of the reflected radiation is changed by replacing tf with tw and rf with rw. That is to say, the case where the radiation is incident from the side of the interference filter F is different from the case where the radiation is incident from the side of the window of the gas cell S.

It is found from the above described matters that since both the window W of the gas cell S and the interference filter F have a high transmittance and a low reflectance for the radiation of a component to be measured, the quantity of the reflected radiation can be deemed as constant regardless of the direction of the surface upon which the radiation is incident. However, the filter has a low transmittance and a high reflectance for the interfering component radiation, so that the quantity of the radiation reflected toward the side of the radiation source in the case where the radiation is incident from the side of the filter is larger than that in the case where the radiation is incident from the side of the window W of the gas cell S.

If the radiation reflected toward the side of the radiation source is not return by reflecting again by means of a radiation source mirror and the like, there is no difference in quantity of the transmitted radiation regardless of the direction of the surface upon the light is incident.

However, in order to increase the quantity of radiation in fact, a mirror is frequently used with the light source, so that the difference in incident direction always leads to a difference in quantity of transmitted radiation.

$I_o$ designates a quantity of an incident radiation; tw designates a quantity of a transmitted radiation; rw designates a quantity of a reflected radiation by the window W; tf designates a quantity of lights passing through the interference filter F; rf designates a quantity of a reflected radiation by the interference filter F; c designates a concentration of a gas contained in the cell S; l designates a length of the cell S; and $\epsilon$ designates a constant determined by the gas.

Accordingly, referring to FIG. 2 and FIG. 4, a comparatively large quantity of interfering component radiation reflected by the interference filters 7a, 7b is reflected by the inside surface of the reference cell 1 or the sample cell 2, the windows of the reference cell 1 and the sample cell 2, reflecting mirrors of the light sources 4a, 4b and the like to arrive at the interference filters 7a, 7b again. This is repeated.

Moreover, since the interference filters 7a, 7b are disposed between the reference cell 1 and the sample cell 2 and the detector 5, a large quantity of the interfering component radiation is reflected by the inside surface of the reference cell 1 and the sample cell 2 to increase an oblique component incident upon the interference filters 7a, 7b. In general, a transmission spectrum of the interference filter has physical characteristics of shifting toward shorter wavelengths in the case of an oblique incidence. Accordingly, as a result, a problem occurs in that the quantity of the interfering component radiation passing through the interference filters 7a, 7b to enter the detector 5 is increased which lowers the accuracy of analysis.

Next, an infrared gas analyzer shown in FIG. 3 has no problem in the reflection of the interfering component radiation in the interference filter since the radiation having wavelength within the absorption bands of the interfering component gases are absorbed by the gas filter 8.

However, in the case where the degree of absorption of the interfering component radiation is slightly lower and a plurality of kinds of interfering component gases are contained in the sample gas, it is difficult to absorb all interfering component radiation, so that the quantity of the interfering component radiation incident upon the detector 5 is comparatively increased which lowers the accuracy of analysis.

An interference-compensation type gas analyzer shown in FIG. 4 can improve an accuracy of analysis since the influences of the interfering component radiation are compensated by the subtractor 10.

However, an interference-compensation detector 5b and a compensation-signal treatment circuit are excessively required, so that a problem occurs in an increase of cost.

SUMMARY OF THE INVENTION

The present invention solves the above described problems and it is an object of the present invention to provide an infrared gas analyzer capable of removing influences of interfering component gases inexpensively to carry out a highly accurate analysis.

An infrared gas analyzer according to the present invention is an infrared gas analyzer, in which a radiation source if disposed on one side of a gas cell and a detector is disposed on the other side of the gas cell. The present invention is also characterized by an interference filter passing radiation having a wavelength within absorption bands of a gas to be measured therethrough, and reflecting radiation having wavelengths within other wavelength ranges, and a gas filter cell absorbing at least radiation having wavelengths within an absorption wavelength range of the interfering component gases, all of which are disposed between the radiation source and the gas cell with the gas filter cell on a side of the radiation source.

With this present infrared gas analyzer, the radiation emitted from the radiation source is incident upon the gas cell through the gas filter cell and the interference filter to nearly equalize the wavelength range of the radiation incident upon the gas cell to the absorption bands of the sample gas to be measured, whereby the influences of the interfering component gases contained in the sample gas within the gas cell are substantially removed.

That is to say, the radiation emitted from the radiation source is at first passed through the gas filter cell to absorb the interfering component radiation. And, the interfering component radiation arriving at the interference filter and not absorbed in the gas filter cell is reflected by the interference filter. The interfering component radiation reflection by this interference filter enters the gas filter cell again to be absorbed. The interfering component radiation, which is not absorbed by the gas filter cell, is reflected by the window of the gas filter cell and the reflecting mirror of the radiation source and passes through the gas filter cell to be reflected by the interference filter again. The above described process and the like are repeated. The interfering component radiation is attenuated to a minimum during the repeated processes to reduce the quantity of the interfering component light incident upon the detector.

DESCRIPTION OF THE PREFERRED EMBODIMENTS

A preferred embodiment of an infrared gas analyzer according to the present invention is described with reference to FIG. 1.

Figure 1:
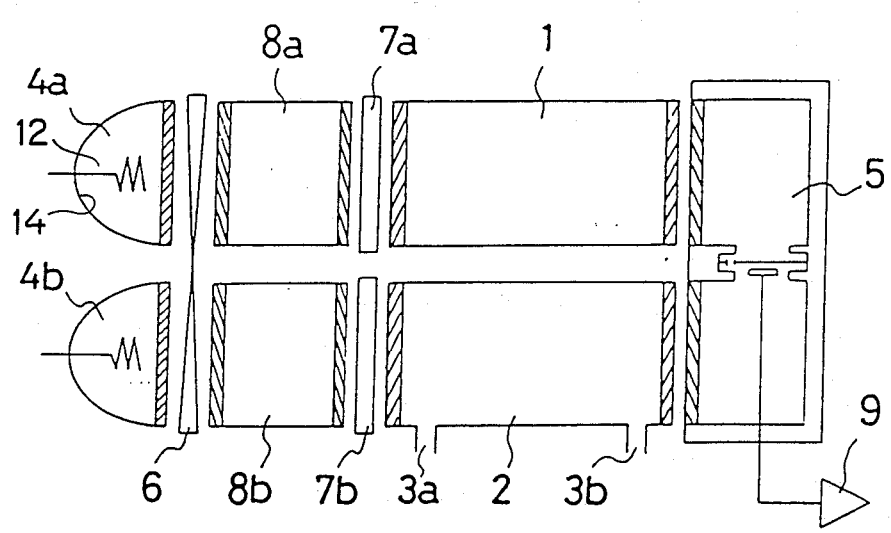
FIG. 1 is a sectional view showing a preferred embodiment of the present invention.

Referring now to FIG. 1, reference numeral 1 designates a reference cell with a reference gas enclosed therein and a sample cell 2 to be supplied with a sample gas is disclosed in parallel to the reference cell 1. The sample cell 2 is provided with a supply port 3a for supplying the sample gas and an exhaust port 3b for exhausting the sample gas. Reference numerals 4a, 4b designate a radiation source disposed on one side of the reference cell 1 and the sample cell 2, respectively. Reference numeral 5 designates a detector, such as condenser microphone, disposed on the other side of the reference cell 1 and the sample cell 2.

Reference numeral 6 designates a chopper disposed in front of the light sources 4a, 4b. The respective light sources 4a, 4b include a filament 12 for generating radiation and a reflector 14 for directing the radiation. Reference numerals 7a, 7b designate an interference filter disposed between the reference cell 1 and the radiation source 4a and between the sample cell 2 and the radiation source 4b, respectively. Gas filter cells 8a, 8b are disposed between the interference filter 7a and the chopper 6 and between the interference filter 7b and the chopper 6, respectively. Reference numeral 9 designates a preamplifier.

The interference filters 7a, 7b pass radiation having wavelengths within absorption bands of a gas to be measured and reflect radiation having wavelengths within other wavelength ranges, while the gas filter cells 8a, 8b absorb radiation having wavelengths within absorption bands of an interfering component gas.

With this infrared gas analyzer, radiation such as light beams emitted from the light sources 4a, 4b is incident upon the reference cell 1 and the sample cell 2 through the gas filter cells 8a, 8b and the interference filters 7a, 7b by means of the chopper 6 in the form of intermittent light. The gas is analyzed on the basis of a difference between a quantity of radiation incident upon the detector 5 through the reference cell 1 and that incident upon the detector 5 through the sample cell 2.

Radiation having the wavelengths within the absorption bands of the gas to be measured of the radiation emitted from the light sources 4a, 4b pass through the gas filter cells 8a, 8b and the interference filters 7a, 7b to be incident upon the detector 5.

On the other hand, the interfering component radiation is first absorbed by the gas filter cells 8a, 8b but the interfering component radiation, which has passed through the gas filter cells 8a, 8b, is reflected by the interference filters 7a, 7b to be incident upon the gas filter cells 8a, 8b, again followed by being absorbed. Also the radiation which passed through the reference cell 1 and the sample cell 2 and was reflected by the reflecting mirror of the light sources 4a, 4b, of the interfering component radiation reflected by the interference filters 7a, 7b, is absorbed by the gas filter cells 8a, 8b again. This process is repeated. The radiation is attenuated during the repeated process.

That is to say, since the interfering component radiation is first absorbed and reduced during the passage thereof through the gas filter cells 8a, 8b, the quantity of the interfering component radiation reflected by the interference filters 7a, 7b is reduced, and then reflected by the interference filters 7a, 7b to be absorbed by the gas filter cells 8a, 8b again, the quantity of the interfering component radiation is still more reduced. Accordingly, as shown by the equation (2), even though the interfering component radiation passing through the interference filters 8a, 8b due to an incident angle upon the interference filters 7a, 7b is generated, its quantity is remarkably reduced, so that the gas can be analyzed with high accuracy.

Figure 2:
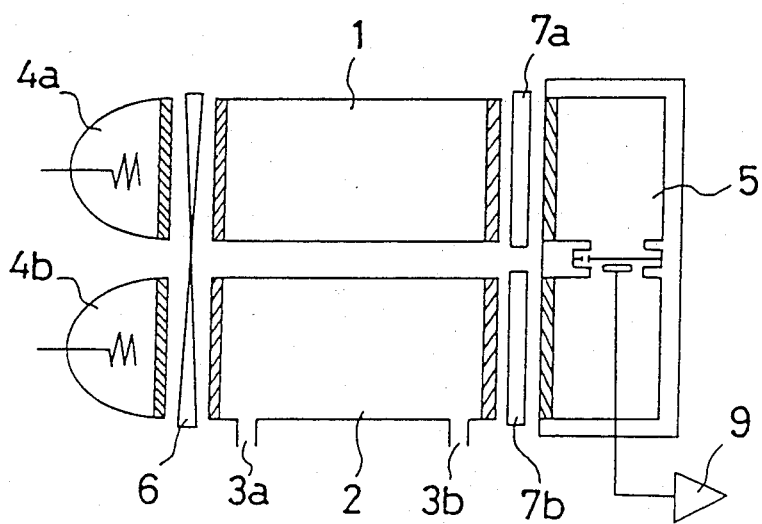
FIGS. 2 to 4 are sectional views showing different conventional examples, respectively.
Figure 3:
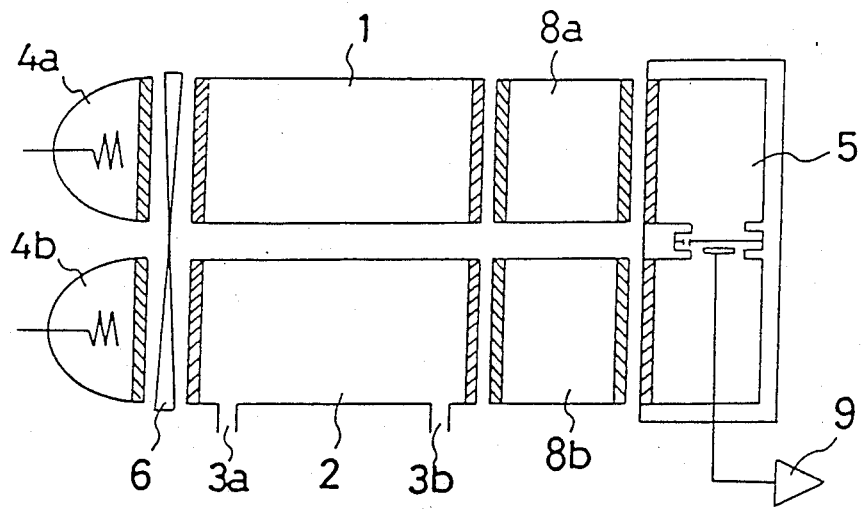
Figure 4:
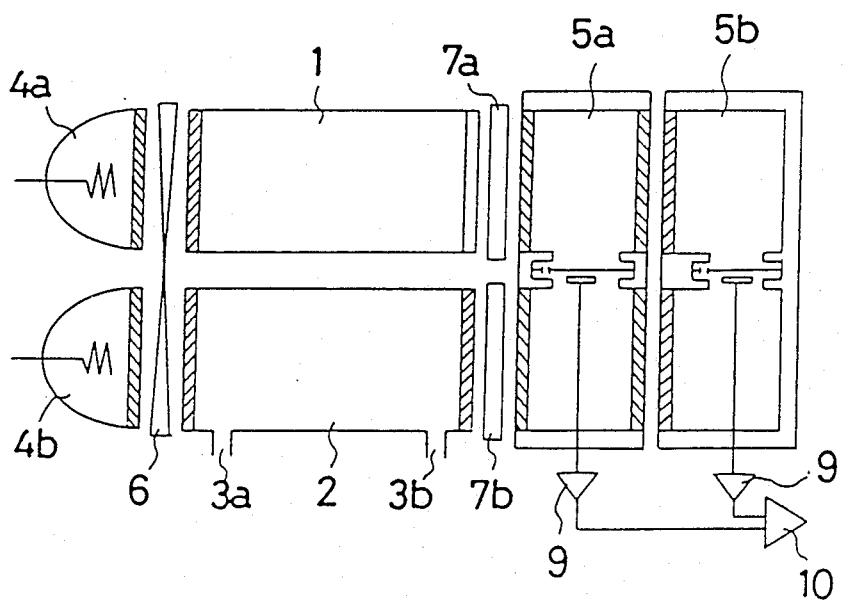
Figure 5:
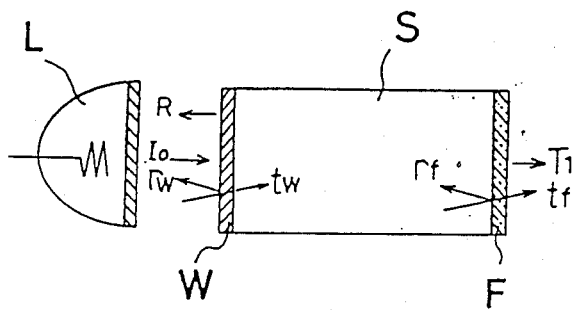
FIG. 5 is a diagram for describing problems of the conventional example.

And, since the interference filters 7a, 7b are disposed closer to the light sources 4a, 4b than the reference cell 1 and the sample cell 2, and the interfering component radiation, which passed through the gas filter cells 8a, 8b, is immediately reflected by the interference filters 7a, 7b, an oblique component resulting from the reflection on the inside surface of the reference cell 1 and the sample cell 2 is reduced in comparison with that in the case where the interference filter is disclosed closer to the detector than the gas cell, as in the conventional example shown in FIG. 2. Thereby, the interfering component radiation incident upon the detector 5 can be still more surely reduced.

Figure 6:
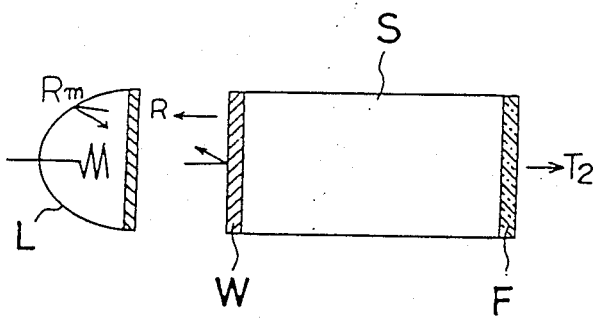
FIG. 6 is a diagram describing a quantity of light incident upon a detector according to the present invention.

In addition, as shown in FIG. 6, a quantity of radiation $T_2$ incident upon the detector 5, and where also a quantity of radiation Rm reflected by the reflecting mirror of the light source 4a is taken into consideration, is expressed by the following equation from the equations (1), (2).

$$T_2 = T_1/(1 - RRm)$$

Since the gas filter cells 8a, 8b are disposed between the light sources 4a, 4b and the interference filters 7a, 7b under such conditions, the interfering component radiation is reflected toward the gas filter cells 8a, 8b by means of the interference filters 7a, 7b having a high reflectance of 99.99% or more and also by means of the reflecting mirror 14 of the light sources 4a, 4b having a reflectance of about 98.5%, respectively, which interfering component radiation is to be absorbed by the gas filter cells 8a, 8b, thus being attenuated.

That is to say, an action of the interference filters 7a, 7b and an action of the gas filter cells 8a, 8b are synergistically utilized to remarkably reduce the quantity of the interfering component radiation incident upon the detector 5, whereby the accuracy of analysis of the gas can be remarkably improved.

CO was measured by means of the infrared gas analyzer (A) shown in FIG. 1 and the conventional infrared gas analyzer (B) shown in FIG. 2. The influenced value by $CO_2$ in the case, where $CO_2$ is contained in the gas to be measured at a ratio of 14% by volume as the interfering component gas, was as follows:

| Influenced Value by $CO_2$ | Ratio of Influenced Value | S/N Ratio |
| --- | --- | --- |
| (A) 35 ppm | 0.16 | 0.69 |
| (B) 225 ppm | 1 | 1 |

It is obvious also from the above described experimental results that the influence by the interfering component radiation in the infrared gas analyzer according to the preferred embodiment shown in FIG. 1 is remarkably reduced in comparison with that in the conventional infrared gas analyzer.

Since the infrared gas analyzer according to the present invention comprises the interference filters for reflecting the interfering component radiation and the gas filters for absorbing the interfering component radiation, both of which are disposed between the radiation source and the gas cell while positioning the gas filter cells on the side of the radiation source, the interfering component radiation in the radiation incident upon the gas cell from the radiation source is first absorbed by the gas filter. And, the interfering component radiation, which was not absorbed by the gas filter cell, is reflected by the interference filter to be incident upon the gas filter cell again, whereby it is absorbed. The interfering component radiation, which passed through the gas filter cell again, is reflected by the reflecting mirror of the radiation source and the like to be further incident upon the gas filter cell, whereby it is absorbed. This process is repeated. The interfering component radiation is attenuated during the repeated process.

Accordingly, the interfering component radiation passing through the gas filter cell and the interference filter and incident upon the detector through the gas cell can be reduced to a minimum.

And, since the gas filter cell and the interference filter are disposed between the radiation source and the gas cell, a large quantity of interfering component radiation is not incident upon the gas cell and not reflected by the inside surface of the gas cell.

Accordingly, no significant problem occurs, such as a large quantity of interfering component radiation being reflected on the inside surface of the gas cell to increase a quantity of the oblique component permeable to the interference filter, which is incident upon the detector through the interference filter, as in the case where the interference filter is disposed between the gas cell and the detector, whereby the quantity of the interfering component radiation passing through the interference filter can be remarkably reduced, and as a result, the accuracy of gas analysis can be still more improved.

What is claimed is:

1. In an improved infrared gas analyzer, the improvement comprising:
    a light source for providing radiation including a desired spectrum of infrared radiation;
    a sample gas cell for receiving and containing a specimen of gas to be analyzed;
    a first gas filter cell having a predetermined charge of a gas capable of absorption of wavelengths of radiation from the light source outside the desired spectrum of infrared radiation;
    a first interference filter designed to reflect wavelengths of radiation from the light source outside the desired spectrum of infrared radiation while passing the desired spectrum of infrared radiation;
    a detector for measuring the absorption of the spectrum of infrared radiation within the sample gas cell, and
    means for positioning the first gas filter cell and first interference filter, respectively, in that order between the light source and the sample gas cell, whereby a repetitive attenuated absorption of radiation outside the desired spectrum of infrared radiation can be accomplished by an initial absorption in the first gas filter cell, the reflection of the first interference filter, and the subsequent absorption of the reflected radiation by the first gas filter cell.

2. The analyzer according to claim 1 further including a reference cell and an associated second interference filter with a second gas filter cell.

3. The analyzer according to claim 2 wherein said gas cell, first interference filter, and first gas filter cell are positioned in parallel with said reference cell, second interference filter, and second gas filter cell.

4. The analyzer according to claim 1 further including reflecting means at said light source for reflecting radiation outside the desired spectrum into said first gas filter cell.

5. In an infrared gas analyzer having a gas cell, a reference cell disposed parallel to said gas cell, a light source at a first side of said gas cell and reference cell, and a detector at a second side of said gas cell and reference cell, an improved interfering component light attenuation system, comprising:
    a filtering means for repeatedly passing light having wavelengths within absorption bands of a gas to be measured and also for repeatedly reflecting light having wavelengths outside of said absorption bands, said filtering means being positioned immediately adjacent said first side of said gas cell and reference cell;
    an absorbing means for repeatedly absorbing light having wavelengths within absorption bands of an interfering component gas, said absorbing means being intermediate said light source and filtering means; and
    a reflecting means for repeatedly reflecting light from said filtering means and absorbing means and back to said filtering means and absorbing means, said reflecting means being located at said light source.

6. The improved system of claim 5 further including a chopper intermediate said light source and absorbing means.

7. The improved system of claim 5 wherein said absorbing means absorbs light coming from said light source, from said reflecting means, and from said filtering means.

8. The improved system of claim 7 wherein said filtering means has a reflectance factor of about 99.9%.

9. The improved system of claim 8 wherein said reflecting means has a reflectance factor of about 98.5%.

10. A method of minimizing the effects of any contaminating interfering gases in an infrared gas analyzer using a light source for providing radiation, a sample cell for holding a test specimen, a first gas filter cell, a first interference filter, and a detector, comprising the steps of:
    directing radiation from the light source through, sequentially, the first gas filter cell, the first interference filter, and the sample cell;
    initially absorbing wavelengths of radiation in the first gas filter that are beyond a desired spectrum that enables an analysis within the sample cell;
    passing wavelengths of radiation within the desired spectrum through the interference filter while reflecting any other wavelengths of radiation back into the first gas filter cell, and
    subsequently absorbing the other wavelengths of radiation in the gas filter cell, whereby undesirable wavelengths of radiation are attenuated to improve the accuracy of the analysis of the test specimen by the desired spectrum of radiation.

11. The method of minimizing influenced results according to claim 10 further including the steps of repeating the steps of reflecting light and absorbing light.

12. The method of minimizing influenced results according to claim 11 wherein the step of reflecting light occurs when light is incident to said light source and also to said gas cell.

13. The method of minimizing influenced results according to claim 12 wherein the steps of reflecting light and absorbing light also occur with respect to a reference cell.

* * * * *